(12) United States Patent
Fenner et al.

(10) Patent No.: US 10,277,407 B2
(45) Date of Patent: Apr. 30, 2019

(54) KEY-ATTESTATION-CONTINGENT CERTIFICATE ISSUANCE

(71) Applicant: Microsoft Technology Licensing, LLC, Redmond, WA (US)

(72) Inventors: Christopher Edward Fenner, Seattle, WA (US); Peter David Waxman, Seattle, WA (US); Gabriel Fortunato Stocco, Redmond, WA (US); Kam Kouladjie, Woodinville, WA (US); Cristian Stefan Salvan, Redmond, WA (US); Prabu Raju, Kirkland, WA (US); Himanshu Soni, Bothell, WA (US); Giridhar Viswanathan, Redmond, WA (US)

(73) Assignee: Microsoft Technology Licensing, LLC, Redmond, WA (US)

( * ) Notice: Subject to any disclaimer, the term of this patent is extended or adjusted under 35 U.S.C. 154(b) by 393 days.

(21) Appl. No.: 15/248,463

(22) Filed: Aug. 26, 2016

(65) Prior Publication Data
US 2017/0302459 A1    Oct. 19, 2017

Related U.S. Application Data

(60) Provisional application No. 62/324,747, filed on Apr. 19, 2016.

(51) Int. Cl.
*H04L 9/32* (2006.01)
*H04L 9/08* (2006.01)
(Continued)

(52) U.S. Cl.
CPC ............ *H04L 9/3268* (2013.01); *G06F 19/00* (2013.01); *G06F 21/57* (2013.01); *H04L 9/0819* (2013.01);
(Continued)

(58) Field of Classification Search
CPC ..................................................... H04L 9/3268
See application file for complete search history.

(56) References Cited

U.S. PATENT DOCUMENTS

| 7,424,610 B2 | 9/2008 | Ranganathan |
| 7,467,370 B2 | 12/2008 | Proudler et al. |

(Continued)

FOREIGN PATENT DOCUMENTS

EP      1873668 A1    1/2008

OTHER PUBLICATIONS

Harris, et al., "StaticTrust: A Practical Framework for Trusted Networked Devices", In Proceedings of the 44th Hawaii International Conference on System Sciences, Jan. 4, 2011, 10 pages.

(Continued)

*Primary Examiner* — William S Powers

(57) ABSTRACT

The present invention provides for streamlined issuance of certificates and other tokens that are contingent on key attestation of keys from a trusted platform module within a computing platform. Various methods are described for wrapping the requested token in a secret, such as an AES key, that is encrypted to a TPM based key in a key challenge. If the requesting platform fails the key challenge, the encrypted certificate or token cannot be decrypted. If requesting platform passes the challenge, the encrypted certificate or token can be decrypted using the AES key recovered from the key challenge.

20 Claims, 10 Drawing Sheets

(51) Int. Cl.
  *H04L 29/06* (2006.01)
  *G06F 21/57* (2013.01)
  *G06F 19/00* (2018.01)
(52) U.S. Cl.
  CPC ............ *H04L 9/0825* (2013.01); *H04L 9/321* (2013.01); *H04L 9/3213* (2013.01); *H04L 9/3234* (2013.01); *H04L 9/3247* (2013.01); *H04L 9/3271* (2013.01); *H04L 63/0823* (2013.01)

(56)  References Cited

U.S. PATENT DOCUMENTS

| | | | |
|---|---|---|---|
| 7,814,535 | B1 | 10/2010 | Barile et al. |
| 8,176,336 | B1 | 5/2012 | Mao et al. |
| 2005/0021968 | A1 | 1/2005 | Zimmer et al. |
| 2005/0149722 | A1 | 7/2005 | Wiseman et al. |
| 2006/0256105 | A1 | 11/2006 | Scarlata et al. |
| 2007/0094719 | A1 | 4/2007 | Scarlata |
| 2007/0101138 | A1* | 5/2007 | Camenisch ........... H04L 9/3234 713/168 |
| 2007/0143629 | A1* | 6/2007 | Hardjono ............ H04L 63/0823 713/189 |
| 2007/0239990 | A1* | 10/2007 | Fruhauf ................. G06F 21/32 713/185 |
| 2008/0059799 | A1 | 3/2008 | Scarlata |
| 2010/0082987 | A1* | 4/2010 | Thom .................... G06F 21/34 713/171 |
| 2011/0099367 | A1* | 4/2011 | Thom .................. H04L 9/0877 713/156 |
| 2012/0163589 | A1 | 6/2012 | Johnson et al. |
| 2014/0108784 | A1 | 4/2014 | Pendarakis et al. |
| 2015/0052610 | A1 | 2/2015 | Thom et al. |
| 2015/0134942 | A1 | 5/2015 | Novak et al. |

OTHER PUBLICATIONS

"Hardware Security for a Worldly-Wise Internet of Things", Published on: Apr. 16, 2015, 3 pages, http://www.digikey.com/en/articles/techzone/2015/apr/hardware-security-for-a-worldly-wise-internet-of-things.

Clercq, Jan De., "Trusted Platform Module (TPM) Key Attestation", Published on: Mar. 19, 2015, 6 pages, http://windowsitpro.com/windows/trusted-platform-module-tpm-key-attestation.

Lee-Thorp, Andrew., "Attestation in Trusted Computing: Challenges and Potential Solutions", In Technical Report RHUL-MA-2010-09, Mar. 31, 2010, 79 pages.

Bond, et al., "The Trusted Platform Module Explained", Published on: Sep. 12, 2011, 5 pages, http://www.cryptomathic.com/news-events/blog/the-trusted-platform-module-explained.

PCT International Search Report and Written Opinion in International Application PCT/US2017/028367, dated Jul. 27, 2017, 15 pages.

"TCG: TCG Infrastructure Working Group A CMC Profile for AIK Certificate Enrollment", Mar. 24, 2011, retrieved from the Internet: http://www.trustedcomputinggroup.org/wp-content/uploads/IWG_CMC_Profile_Cert_enrollment_v1_r7.pdf, retrieved on Nov. 29, 2016, 72 pages.

"TCG: TCG Infrastructure Working Group Reference Architecture for Interoperability (Part 1)", Jun. 16, 2005, retrieved from the Internet: http://www.trustedcomputinggroup.org/files/resourse_files/8770A217-1D09-3519-AD17543F6163205/IWG_Architecture_v1_0_r1.pdf, retrieved on Oct. 4, 2011, 66 pages.

* cited by examiner

Conventional Key Attestation

CONVENTIONAL HEALTH ATTESTATION

KEY-ATTESTATION-CONTINGENT CERTIFICATE ISSUANCE

RELATED APPLICATIONS

The present application claims priority of U.S. patent application Ser. No. 62/324,747, filed Apr. 19, 2016, entitled "Health Certificate based on Key Attestation and Health Attestation" which is hereby incorporated by reference.

BACKGROUND

Computing systems today are increasingly exposed to security threats that may compromise data stored on the systems and functionality of the systems themselves. For instance, a computing device can be infected with malware that enables unauthorized access to data stored on the device, and/or that can enable functionality of the device to be hijacked by an unauthorized party.

Trusted Platform Modules (TPM) help improve security for computing systems. A TPM is a computer chip (microcontroller) that is typically part of a computer's motherboard. TPMs provide for hardware-based authentication and attestation. Authentication is a process for proving that a computing device is what it claims to be. Attestation is a process for proving that a computing device is trustworthy and has not been breached.

Generally, a TPM represents a secure processing environment that can be leveraged to store security assets, such as security keys, certificates, and passwords, that are used to authenticate a platform (e.g., computing devices, mobile devices, network equipment). Further, a TPM can be utilized to store measurements of valid device states (e.g., operating system states), which can be used to ascertain whether a current device state has been compromised such that the device may be unsecure and/or untrusted.

The trusted platform module (TPM) can be used to create cryptographic public/private key pairs in such a way that the private key can never be revealed or used outside the TPM. This type of key can be used to guarantee that a certain cryptographic operation occurred in the TPM of a particular computer by virtue of the fact that any operation that uses the private key of such a key pair must occur inside that specific TPM.

Encryption, Digital Signatures, and Certificates

Encryption typically works by using a private key/public key pair (referred to as "public key cryptography" or "PKI"). Data that is encrypted with one key can be decrypted only with the other key from the key pair. The keys in the key pair are similar. Generally, the keys are based on prime numbers and have a sufficient length (e.g., bits) to make it extremely difficult to decrypt data without the correct key. One key is kept secret (the private key) and the other key (the public key) is distributed. Anybody with the public key can encrypt data that then can be decrypted only by the holder of the corresponding private key.

Key pairs can also be used for digital signatures to certify that a message is coming from who it is supposed to be coming from. The owner of the keys signs the data with the private key. The receiver of the data can compare the signature against the public key, and if they match, have proof as to the identity of the sender of the message.

For public-key cryptography to be valuable, users must be assured that the other parties with whom they communicate are "safe"—that is, their identities and keys are valid and trustworthy. To provide this assurance, users must have a registered identity. These identities are stored in a digital format known as a certificate. Certification Authorities (CAs) represent the people, processes, and tools to create these digital certificates that securely bind the names of users to their public keys. In creating certificates, CAs act as agents of trust. As long as users trust a CA and its business policies for issuing and managing certificates, they can trust certificates issued by the CA. CAs create certificates for users by digitally signing a set of data that includes the following information, among other things:

- the user's name in a distinguished name format;
- a public key of the user;
- the validity period (or lifetime) of the certificate (a start date and an end date); and
- the specific operations for which the public key is to be used (whether for encrypting data, verifying digital signatures, or both).

The CA's signature on a certificate allows any tampering with the contents of the certificate to be easily detected. As long as the CA's signature on a certificate can be verified, the certificate has integrity. Since the integrity of a certificate can be determined by verifying the CA's signature, certificates are inherently secure and can be distributed in a completely public manner (for example, through publicly-accessible directory systems).

Users retrieving a public key from a certificate can be assured that the public key is valid. That is, users can trust that the certificate and its associated public key belong to the entity specified by the distinguished name. Users also trust that the public key is still within its defined validity period. In addition, users are assured that the public key may be used safely in the manner for which it was certified by the CA.

TPM Keys

Generally, a TPM has two types of keys: an endorsement key ("EK") and an attestation identity key ("AIK").

The Endorsement Key (EK) is a restricted encryption key (comprising a private/public key pair) that is permanently embedded in the TPM security hardware, generally at the time of manufacture. The EK is the root of the TPM's identity. The private portion of the EK (EKPriv) is never visible outside of the TPM. Because the EK can only be used for encryption, possession of the private EK (EKPriv) can only be proved indirectly, by using it to decrypt a value that has been encrypted with the public EK (EKPub). Therefore, while the EK cannot be used to produce a digital signature, it is able to provide for TPM authentication based on decryption operations. In sum, the private portion of the endorsement key (EKPriv) is never released outside of the TPM. The public portion of the endorsement key (EKPub) helps to recognize a genuine TPM.

The Attestation Identity Key ("AIK") is a restricted signing RSA key (comprising a private/public key pair) that is used to provide platform authentication based on the attestation capability of the TPM. AIKs allow the TPM to produce cryptographically signed attestation evidence (statements) about the operational state of the platform. These signed statements can augment the current Trusted Network Connect (TNC) protocols, making them more resilient to local attacks by malware and to attempts by endpoints to misrepresent their operational state.

Key Attestation

Key attestation or TPM attestation refers to cryptographically proving a key comes from (e.g. is resident in) the TPM of a particular platform or device. A user certificate with a TPM-attested key provides higher security assurance backed up by non-exportability, anti-hammering, and isolation of keys provided by the TPM. For example, with TPM key attestation, an administrator can define the set of devices that users can use to access their corporate resources and have strong guarantees that no other devices can be used to access them. This access control paradigm is strong because it is tied to a hardware-bound user identity.

An EK certificate (which is also resident in a TPM) is used to bind an identity, in terms of specific security attributes, to a TPM.

Real-world uses of the AIK, like health attestation or key attestation, require AIK trust from the entity to whom the device health or key data is being attested. This trust is embodied in an AIK certificate, which is issued from public servers of an AIK Issuance Service. This certificate is proof that the AIK is a Restricted Signing TPM key, and may not be used to sign TPM information (Health attestation or key attestation claims) that are not true. An AIK certificate is used to attest to the presence of an AIK within a TPM. It is also used to attest that other keys certified by the AIK did in fact originate from that particular TPM.

However, current implementations of AIK certificate issuance require two or more network hops or round trips from the client device to the public AIK issuance servers. Current implementations of health certificate issuance require two or more round trips to the AIK issuance servers plus an additional hop or round trip to a health issuance server. Further, some private networks do not grant access to the public AIK certificate issuance servers, so provisioning an AIK certificate (and thus a health certificate) may be impossible on devices restricted to these networks.

It is with respect to these and other general considerations that aspects of the technology have been made. Also, although relatively specific problems have been discussed, it should be understood that the aspects of the technology presented should not be limited to solving the specific problems identified in the background.

SUMMARY OF THE INVENTION

The present invention provides for streamlined issuance of certificates and other tokens (such as decryption keys, signing keys, authentication credentials to login to other systems or websites, and licenses to enable a client-specific features) that are contingent on key attestation, such as, for example, key attestation of keys from a trusted platform module within a computing platform. More specifically, this disclosure teaches systems and methods for obtaining certificates and other tokens that are contingent on key attestation within a single round trip between a requesting client and an issuing server. Various methods are described for wrapping the requested certificate (or other token) in a server key, such as an AES key, that the server encrypts to a public EK in a key challenge. If the EK and AIK keys are not both present on the TPM, the encrypted certificate (or other token) cannot be decrypted. If the keys are present on the TPM, then the certificate (or other token) can be decrypted using the AES key recovered from the key challenge.

In an embodiment, the present invention provides for server-side verification of a client's request for health certificate without the need for an AIK certificate. The client sends a key attestation claim along with a health attestation claim to a server that issues health certificates. The server will create a key attestation challenge that needs to be decrypted by the client to prove the residency of the EK and AIK and, at the same time, the server will also create a health attestation blob that the client needs in order to move forward with health attestation. The server sends this data back to the client. If the key attestation challenge is valid, the client will be able to decrypt the health attestation blob and be in the same state it would have been if the client had possession of an AIK certificate (except that it required only one round trip to the health server and did not require any communications with a public AIK issuance service).

In another embodiment, the present invention provides for server-side verification of a request for an AIK certificate and issuance of this certificate with a single hop or round trip to the AIK issuance server. When the server receives a request for AIK certificate, it creates a key attestation challenge that needs to be decrypted by the client to prove the residency of the EK and AIK and, at the same time, the server will also use a secret (e.g., AES Key or server key) that is wrapped in the key attestation challenge to encrypt the AIK certificate. The server sends this data back to the client. If the key attestation challenge is valid, the client will be able to decrypt the AIK Certificate without the need to send additional proof to the server.

It will be appreciated that these are just a few examples, and other examples are contemplated. Further, while this disclosure describes examples of attestation of key claims and health claims, the present disclosure applies to any server side verification of a TPM claim that involves a key that needs to be attested. Further still, while this disclosure describes issuance of health certificates and AIK certificates, the present disclosure relates to server-side issuance of any certificate or any other token to a client computer, including for example, decryption keys, signing keys, authentication credentials to login to other systems or websites, and licenses to enable client-specific features.

Additionally, this Summary is provided to introduce a selection of concepts that are further described below in the Detailed Description section. This Summary is not intended to identify key features or essential features of the claimed subject matter.

BRIEF DESCRIPTION OF THE DRAWINGS

The detailed description is described with reference to the accompanying figures. In the figures, the left-most digit(s) of a reference number identifies the figure in which the reference number first appears. The use of the same reference numbers in different instances in the description and the figures may indicate similar or identical items.

DETAILED DESCRIPTION

Figure 1:
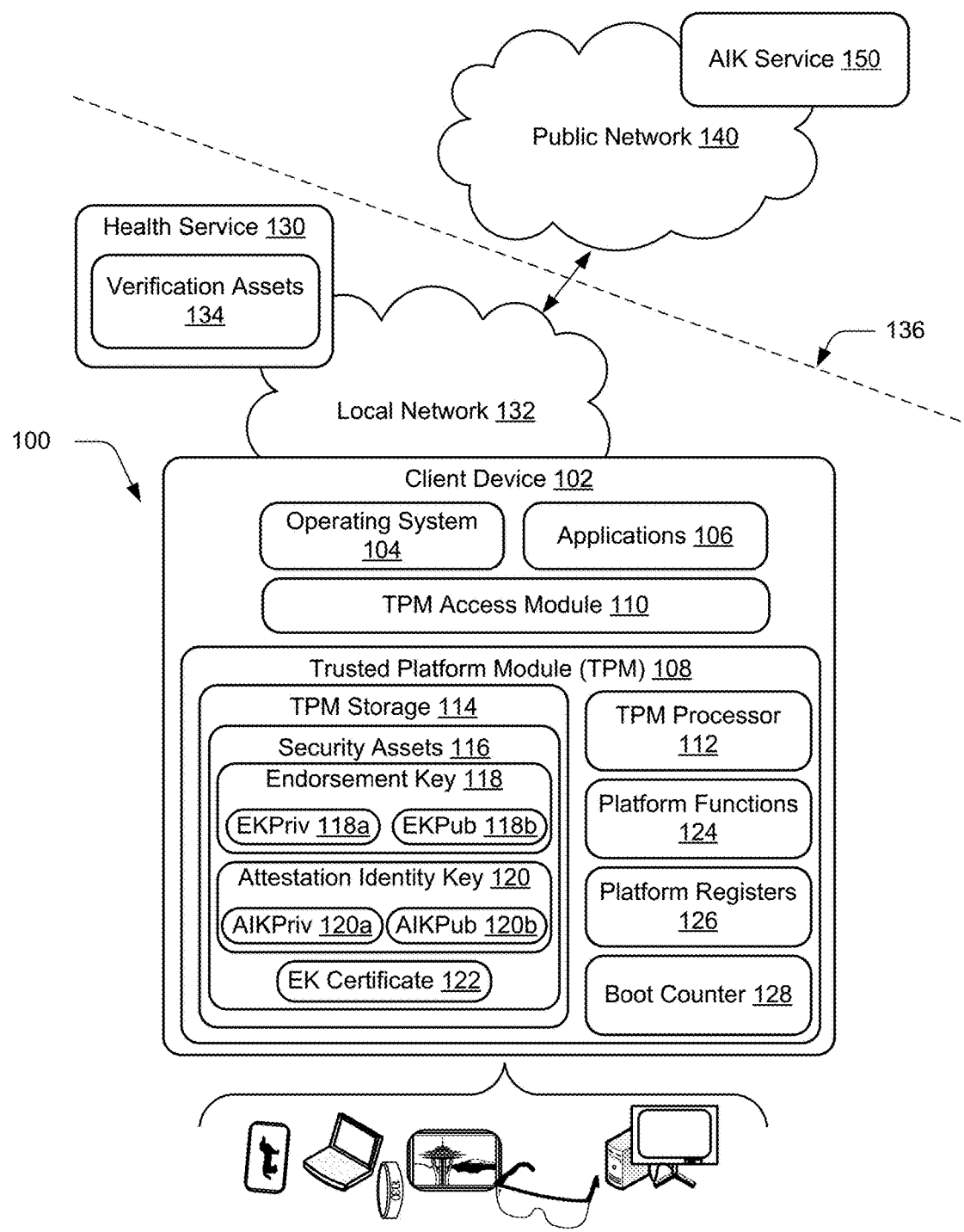
FIG. 1 is an illustration of an environment in an example implementation that is operable to employ techniques discussed herein in accordance with one or more embodiments of the present invention.

FIG. 1 is an illustration of an environment 100 in an example implementation that is operable to employ techniques based on key attestation and health attestation discussed herein.

Environment 100 includes a client device 102 which can be embodied as any suitable device such as, by way of example and not limitation, a smartphone, a tablet computer, a portable computer (e.g., a laptop), a desktop computer, a wearable device, and so forth. One of a variety of different examples of a client device 102 is shown and described below in FIG. 9.

The client device 102 includes a variety of different functionalities that enable various activities and tasks to be performed. For instance, the client device 102 includes an operating system 104 and applications 106. Generally, the operating system 104 is representative of functionality for abstracting various system components of the client device 102, such as hardware, kernel-level modules and services, and so forth. The operating system 104, for instance, can abstract various components of the client device 102 to the applications 106 to enable interaction between the components and the applications 106.

The applications 106 are representative of functionality to enable various tasks and activities to be performed via the client device 102, such as word processing, web browsing, email, social media, enterprise tasks, and so forth. The applications 106 may be installed locally on the client device 102 to be executed via a local runtime environment, and/or may represent portals to remote functionality, such as cloud-based services, web apps, and so forth. Thus, the applications 106 may take a variety of forms, such as locally-executed code, portals to remotely hosted services, and so forth.

The client device 102 further includes a trusted platform module (TPM) 108, which is representative of a portion of the client device 102 that is protected from general access by most or all other functionalities of the client device 102. The TPM 108 can be implemented in various ways, such as a separate, dedicated hardware environment (e.g., a dedicated chip), a subdivided portion of an existing hardware environment (e.g., a sub-portion of a central processing unit (CPU)), a protected firmware environment, and so forth. In one or more implementations, the TPM 108 is a module in accordance with a Trusted Platform Module (TPM) specification available from the Trusted Computing Group (TCG). Those skilled in the art will appreciate that other TPMs may exist. In essence, any protected module may act as a TPM for purposes of this application.

According to various implementations, interaction with the TPM 108 is brokered by a TPM access module 110. Generally, the TPM access module 110 is representative of functionality to enable different components of the client device 102 to interact with the TPM 108, such as components of the operating system 104, the applications 106, and so forth. The TPM access module 110, for instance, represents a device driver for the TPM 108. The TPM access module 110 may be implemented in various ways, such as a component of the operating system 104, a separate system component of the client device 102 (e.g., a kernel level component), combinations thereof, and so forth.

The TPM 108 includes a TPM processor 112 and TPM storage 114. According to various implementations, the TPM processor 112 represents a dedicated hardware processing unit that can be leveraged by the TPM 108 to perform various processing tasks. The TPM storage 114 is representative of data storage capacity for the TPM 108 and that is protected from access by entities external to the TPM 108.

Stored on the TPM storage 114 are security assets 116, which are representative of different types of security-related information that may be leveraged to verify the identities of certain entities, the authenticity and/or trusted status of various types of data, and so forth. Examples of the security assets 116 include security keys (e.g., cryptographic keys), security certificates, encryption and decryption algorithms, protected data, and so forth. In a particular implementation, the security assets 116 include an endorsement key (EK) 118 comprising a private key (EKPriv) 118a and a public key (EKPub) 118b, an attestation identity key (AIK) 120 comprising a private key (AIKPriv) 120a and a public key (AIKPub) 120b, and an endorsement key certificate (EIC) 122. As used herein, the term "AIK" and "AIK 120" may refer to the public key (AIKPub) and/or the private key (AIKPriv). As used herein, the term "EK" and "EK 118") may refer to the public key (EKPub) and/or the private key (EKPriv). Details concerning ways in which the security assets 116 may be configured and leveraged are discussed below.

TPM 108 further includes platform functions 124, platform registers 126, and a boot counter 128. The platform functions 124 represent various functions used for providing secure storage of information, such as authentication functions, key generation functions, encryption and decryption functions, context-related functions, and so forth. According to various implementations, the TPM access module 110 may interact with the platform functions 124 to perform various aspects of techniques for health certificate based on key attestation and Health attestation described herein.

The platform registers 126 represent storage locations for storing system state and context information for the client device 102. For instance, the platform registers 126 may be leveraged to store "measurements" of various system components, such as measurements of modules of the operating system 104 that are collected at a system boot time. In at least some implementations, the platform registers represent platform configuration registers (PCRs) of the TPM 108.

Generally, a "measurement" refers to a way of identifying and/or characterizing various device-related data, such as code modules of the client device 102, configuration data of the client device 102, and so forth. As used herein, the term "code module" generally refers to portions of executable code, such as portions of the applications 106, services, modules of the operating system 104, processes, various binaries and/or executables, and so forth. Examples of measurements include hash values generated from device-related data, data signatures, encrypted versions of device-related data and/or portions of device-related data, and so forth. A measurement, for instance, may be generated by applying a Secure Hash Algorithm (SHA) to device-related data, e.g., SHA-I, SHA-2, and so forth.

The boot counter 128 represents functionality for tracking when the client device 102 is booted and rebooted. For instance, the boot counter 128 maintains a boot value that is modified each time the client device 102 is rebooted. Generally, the boot counter 128 may be leveraged to distinguish between different boot states of the client device 102.

The environment 100 also includes a health service server ("health service") 130, which is communicatively accessible to the client device 102 via a local network 132. Generally, the health server 130 represents a resource that the client device 102 may interact with to enable various trust-related transactions to be performed, such as to obtain a health certificate for the client device 102. The health server 130 can be implemented via various types and/or combinations of computing devices, examples of which are described below in FIGS. 3 and 4.

The local network 132 is representative of a network via which various entities of the environment 100 may communicate. The local network 132 may assume a variety of different configurations, such as a local area network (LAN) for an entity such as an enterprise entity, a government entity, an education entity, and so forth. In at least some implementations, data communicated between the client device 102 and the health server 130 is prevented from being exposed outside of the local network 132 as represented by dashed line 136. For instance, communication between the client device 102 and the health server 130 may be constrained within the local network 132 and is not permitted to traverse to a network outside of the local network 132, such as public network 140.

The health server 130 may include verification assets 134, which represent different security-related assets that enable the health server 130 to verify the validity of certain claims made by the client device 102. Examples of the verification assets 134 include cryptographic keys, certificates, identities of different certificate authorities, and so forth.

An AIK certificate issuance service 150 may be accessible to the client 102 over public network 140. The AIK issuance service may include a certificate authority for issuing AIK Certificates.

Having described an example environment in which the techniques described herein may operate, consider now a discussion of an example TPM key attestation leverages a TPM's Endorsement Key (EK) that is injected into the TPM when it is manufactured and that is unique to each TPM. The trust in the EK is based on the secure and tamper-proof storage of the EK in the TPM and on the fact that the EK's certificate chains to the TPM manufacturer's issuing CA. "Chains" meaning that the EK's certificate can be cryptographically verified by using the certificate of the TPM manufacturer's issuing CA.

Figure 2:
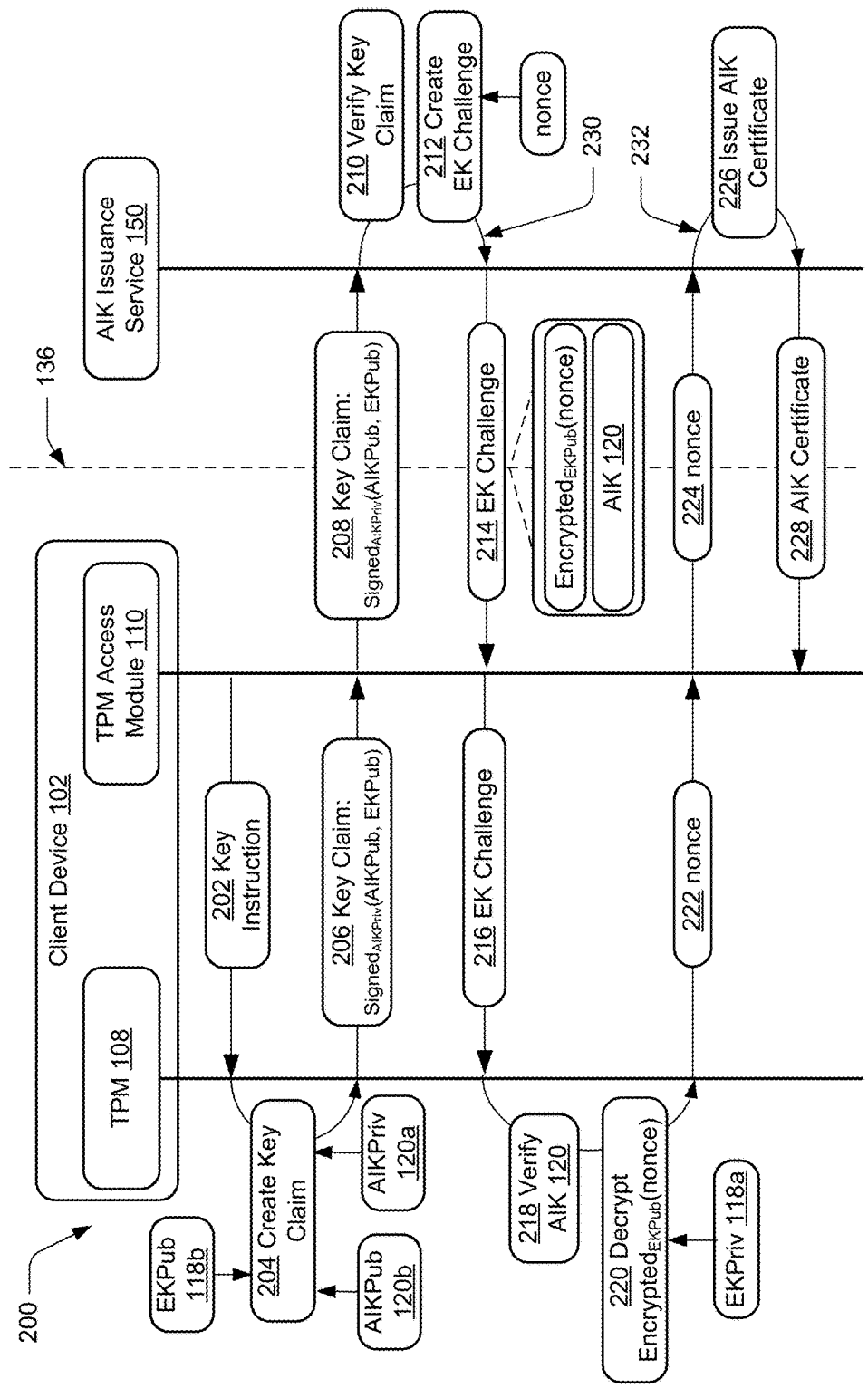
FIG. 2 depicts a conventional implementation of key attestation.

FIG. 2 illustrates a conventional process 200 for TPM key attestation by obtaining an Attestation Identity Key (AIK) Certificate from an AIK service 150, which is located on a public server. At step 202, the TPM access module 110 communicates a key attestation instruction (key instruction) to the TPM 108. Generally, the key instruction 202 instructs the TPM 108 to create a key attestation claim (key claim). In response to receiving the key instruction 202, the TPM 108 executes a key attestation process 204 to generate a key claim, which is used to obtain an AIK certificate that attests that the AIK key 118 is contained within the TPM 108. The key claim includes the public AIK (AIKPub) 120*b* and the public EK (EKPub) 118*b* and is signed using the private AIK (AIKPriv) 120*a*. For instance, the key claim is generated as Signed$_{AIKPriv}$(AIKPub, EKPub). After generating the key claim at step 204, the TPM 108 communicates the key claim to the TPM access module 110 at step 206.

The TPM 110 sends the key claim to a server with an AIK Certificate Authority for verification, such as AIK Issuance Service 150. Server 150 is outside of the local network 132 (shown in FIG. 1) as shown by dashed line 136. At step 210, the server 150 verifies the signature (i.e., AIKPriv) using the AIK public key from the key claim. If the key claim passes verification, the server 150 creates an EK challenge at step 212. The EK challenge is a nonce that is encrypted by the public version of the client 102's EK (EKPub 118*b*) from the key claim. The server 150 sends the EK Challenge to the TPM 108 through the TPM Access Module 110 at steps 214 and 216.

At step 218, the TPM 108 verifies that the AIK 120 in the EK challenge is co-resident in the TPM with the EKPub used to sign the EK Challenge. If so, at step 220, the TPM 108 decrypts the nonce using the EKPriv 118*a* that is resident on the TPM. If the TPM 108 is able to decrypt the nonce, the client 102 will send the decrypted nonce back to the server 150 (through the TPM Access Module 110) at steps 222 and 224 to prove that it passed the attestation check (i.e., that the AIK is resident in the TPM). At that point the server 150 will issue the certificate for the AIK at step 226 and send the AIK Certificate back to the client 102 at step 228. The client will store the AIK Certificate. As shown if FIG. 2, the conventional key attestation process requires two separate round trips from the client 102 to the server 150 as shown by curved arrows 230 and 232.

Figure 3:
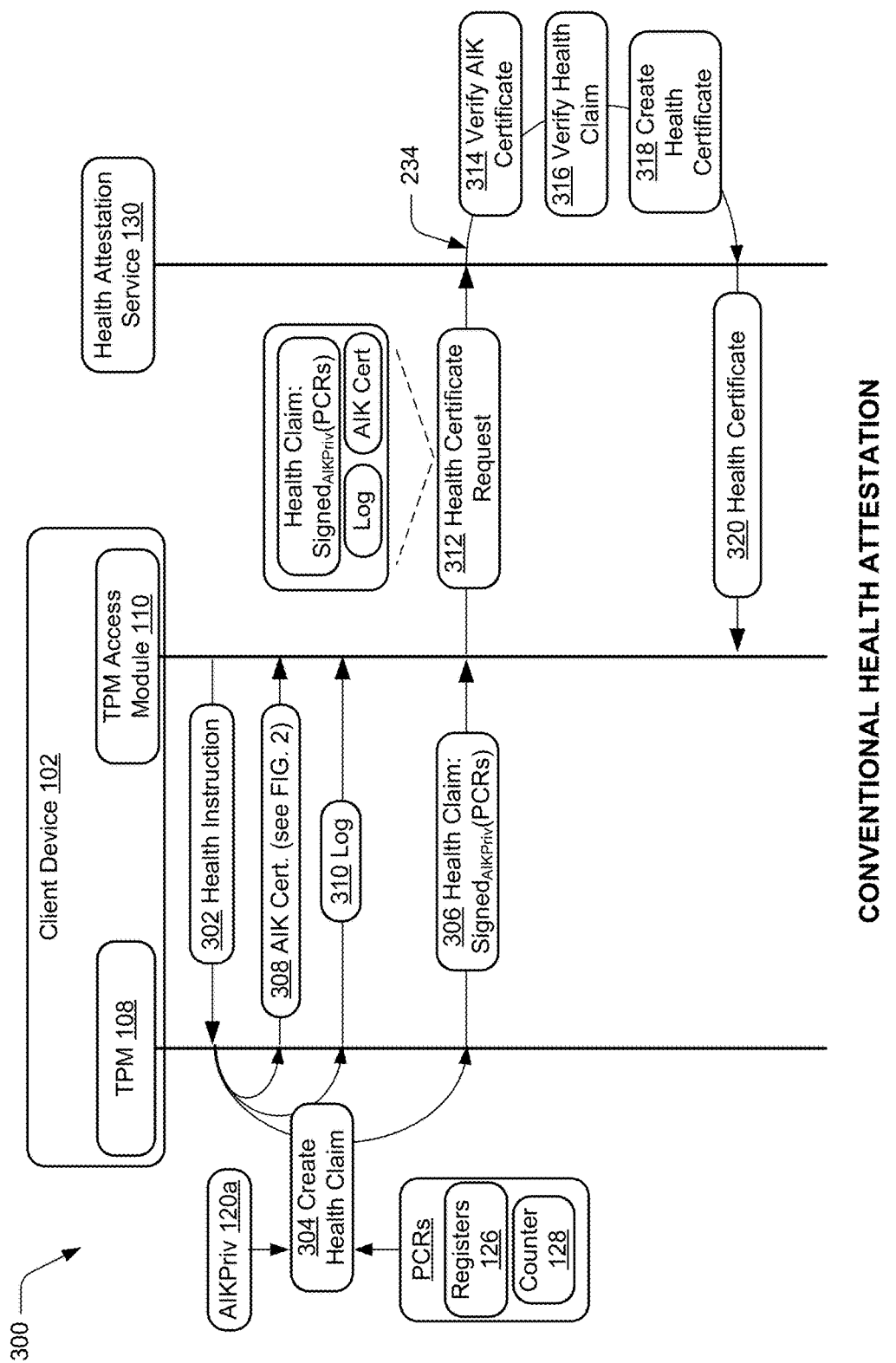
FIG. 3 depicts a conventional implementation of health attestation.

FIG. 3 illustrates a conventional process 300 for Health attestation. The TPM access module 110 communicates a Health attestation instruction (health instruction) to the TPM 108 at step 302. The health instruction instructs the TPM 108 to create a Health attestation claim (health claim). In response at step 304, the TPM 108 generates a health claim that includes a quote (e.g., PCRs) from the platform registers 126 and the boot counter 128 and signs the PCRs using AIKPriv 120*a*. The TPM 108 then communicates the health claim to the TPM access module 110 at step 306. Also in response to the health instruction 302, the TPM 108 sends an AIK Certificate (such as one received using the process shown in FIG. 2) at step 308 and a TCG log at step 310 to the TPM Access Module 110. The TCG log includes measurements of various modules and/or binaries that reside (e.g., stored, loaded, and/or running) on the client device 102. For instance, when a health certificate is requested, measurements of various modules and processes are captured and stored as part of the TCG log.

Next, the TPM access module 110 generates a health certificate request at step 312 that includes the health claim, the log, and the AIK Certificate and sends the certificate request to a Health attestation server 130. The request may be routed using a Uniform Resource Indicator (URI) that identifies the health server 130. The health server 130 is in the same local network 132 as the client device.

The health server 130 receives the health certificate request and performs a verification process 314 to confirm that the AIK Cert was issued by a known and trusted certificate authority (CA) and the AIK certificate is valid and not revoked. It then extracts the AIKPub from the certificate. The server trusts the AIKPub because it came from the AIK Certificate. At step 316, the server 130 determines the validity of the health claim by checking to make sure that the AIK public key (AIKPub) from the AIK Certificate matches the AIKPriv used to sign the health claim. Also at step 316, the server 130 checks the PCRs in the health claim against the log to make sure that they match. In this particular example, the verification process 316 determines that the health claim is valid, and thus the health server 130 generates a health certificate at step 318 that attests to the health status of the client device 102. The health certificate, for instance, identifies the client device 102 and indicates that the client device 102 is currently in a safe state. The server 130 then communicates the health certificate to the client 102 at step 320.

The conventional health attestation process 300 requires three round trips to a server: two round trips from client 102 to the public AIK server 150 and back as shown by arrows 230 (first round trip) and 232 (second round trip) in FIG. 2 plus a third round trip from client 102 to health attestation server 130 and back as shown by arrow 234 in FIG. 3.

Figure 4:
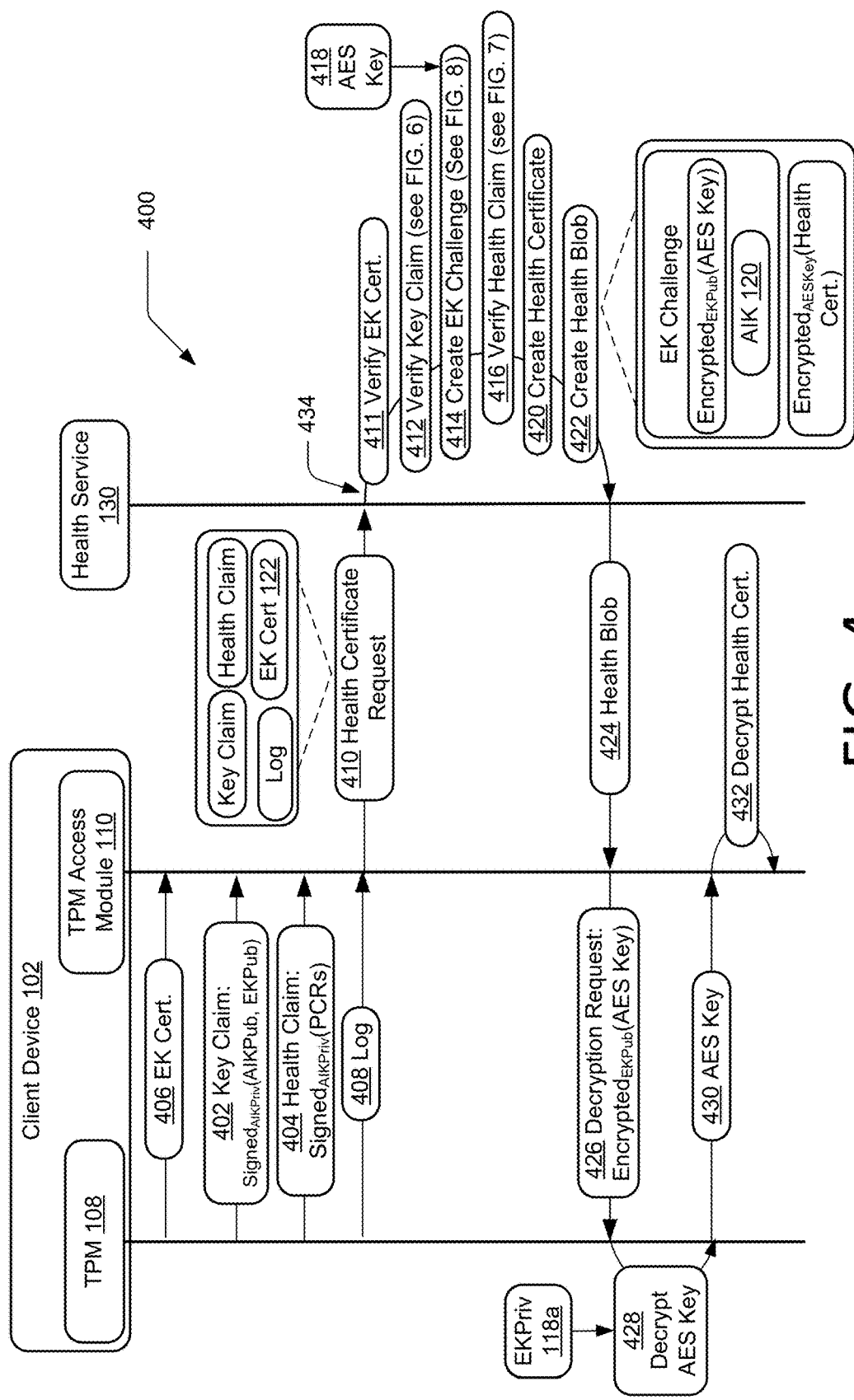
FIG. 4 depicts an example implementation of health attestation in accordance with one or more embodiments of the present invention.

FIG. 4 shows a health attestation process 400 in accordance an embodiment of the present invention. Health attestation process 400 has several advantages over the conventional processes shown in FIGS. 2 and 3. For example, process 400 does not require the client 102 to provide the server 130 an AIK certificate to receive a health certificate. Further, process 400 requires only one hop to a server as shown by arrow 434. Even further, process 400 does not require the client 102 to communicate with any servers or services outside of the local network 132 to receive a health certificate.

Process 400 begins by ascertaining that a health certificate is to be retrieved for a client device. The client device 102, for instance, receives a request from a particular application/service to attest to the health of the client device 102. Alternatively or additionally, the client device 102 initiates a health certificate retrieval process automatically, such as in response to rebooting of the client device 102.

At step 402, the TPM 108 sends a key claim to the TPM Access Module 110. In an embodiment, the key claim is created in response to a key instruction sent from the TPM Access Module 110 to the TPM 108. The key claim may include the AIKPub 120b and the EKPub 118b, which are signed with AIKPriv 120a.

At step 404, the TPM 108 sends a health claim to the TPM Access Module 110. In an embodiment, the health claim is created in response to a health instruction sent from the TPM Access Module 110 to the TPM 108. The health claim may include PCRs, which are signed with AIKPriv 120a.

The TPM Access Module 110 may already have the EK Certificate, but if not, the TPM 108 sends the EK Cert 122 to the TPM Access Module 110 at step 406. At step 408, the TPM 108 sends the TPM Access Module 110 and the TCG log. Although steps 402, 404, 406, and 408 are shown as being sent in a particular order, they may be sent in any order from the TPM 108 to the TPM Access Module 110. Further, these steps can be performed separately or grouped into one or more communications to the TPM Module 110.

The TPM Access Module 110 receives the key claim, the health claim, the log, and the EK certificate 122. The TPM Access Module then creates a health certificate request, which may include the health claim, the key claim, the log, and the EK certificate, and sends this request to the health service server 130 at step 410. In at least some implementations, the request, the key attestation claim, the EK Certificate and the health attestation claim are sent to the health service 130 as part of a single communication from the client device 102.

At step 411, the server extracts the EK certificate from the health certificate request and verifies that the EK cert is issued by a known and trusted CA, that the certificate is valid, and is not revoked. It then extracts the EKPub from the EK certificate.

Figure 6:
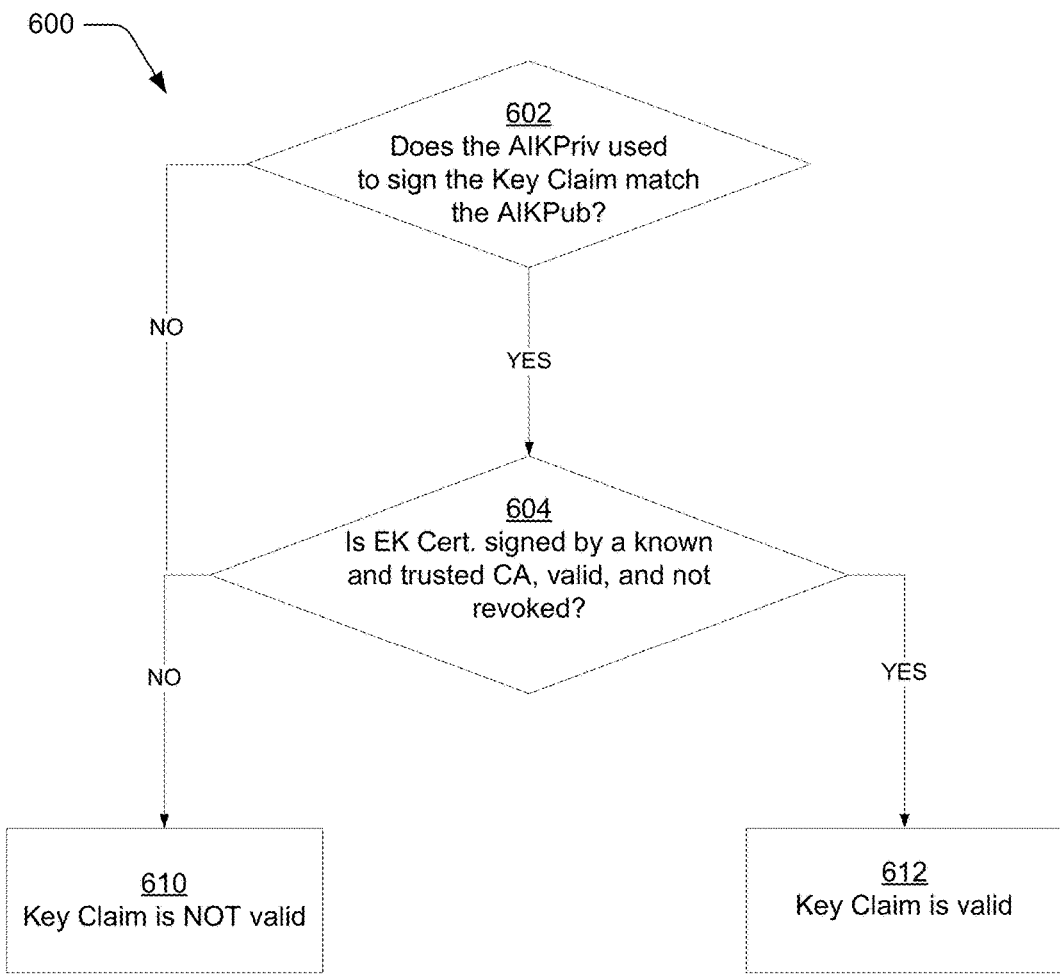
FIG. 6 is a flow diagram that illustrates steps in a method for verifying a key attestation claim in accordance with one or more embodiments of the present invention.

At step 412, the server 130 verifies the key claim as described in detail with regard to FIG. 6. If the verification step 412 passes, the process 400 proceeds to step 414 where it creates an EK challenge.

Figure 8:
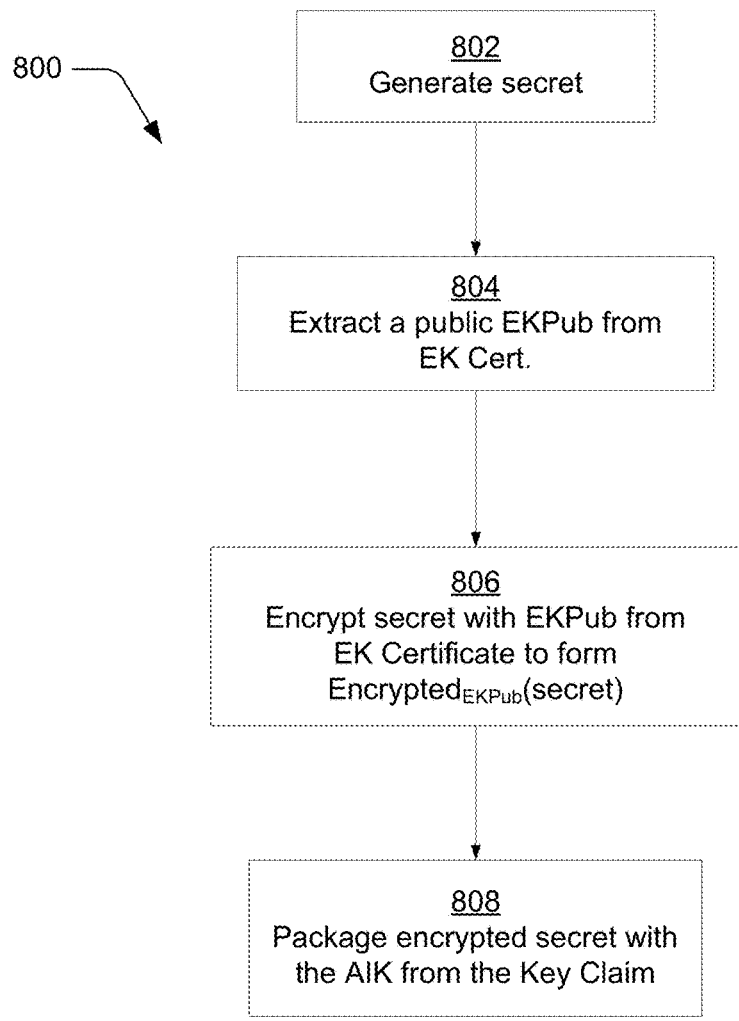
FIG. 8 is a flow diagram that illustrates steps in a method for creating a key challenge in accordance with one or more embodiments of the present invention.

At step 414, the server creates an EK Challenge, which is described in detail with respect to FIG. 8. Generally, this process includes generating a secret, such as an AES key (or server key) 418, encrypting this key using the EKPub 118a that was extracted from the EK certificate in step 411, and then packaging this together with the AIKPub key received in the Key claim.

Figure 7:
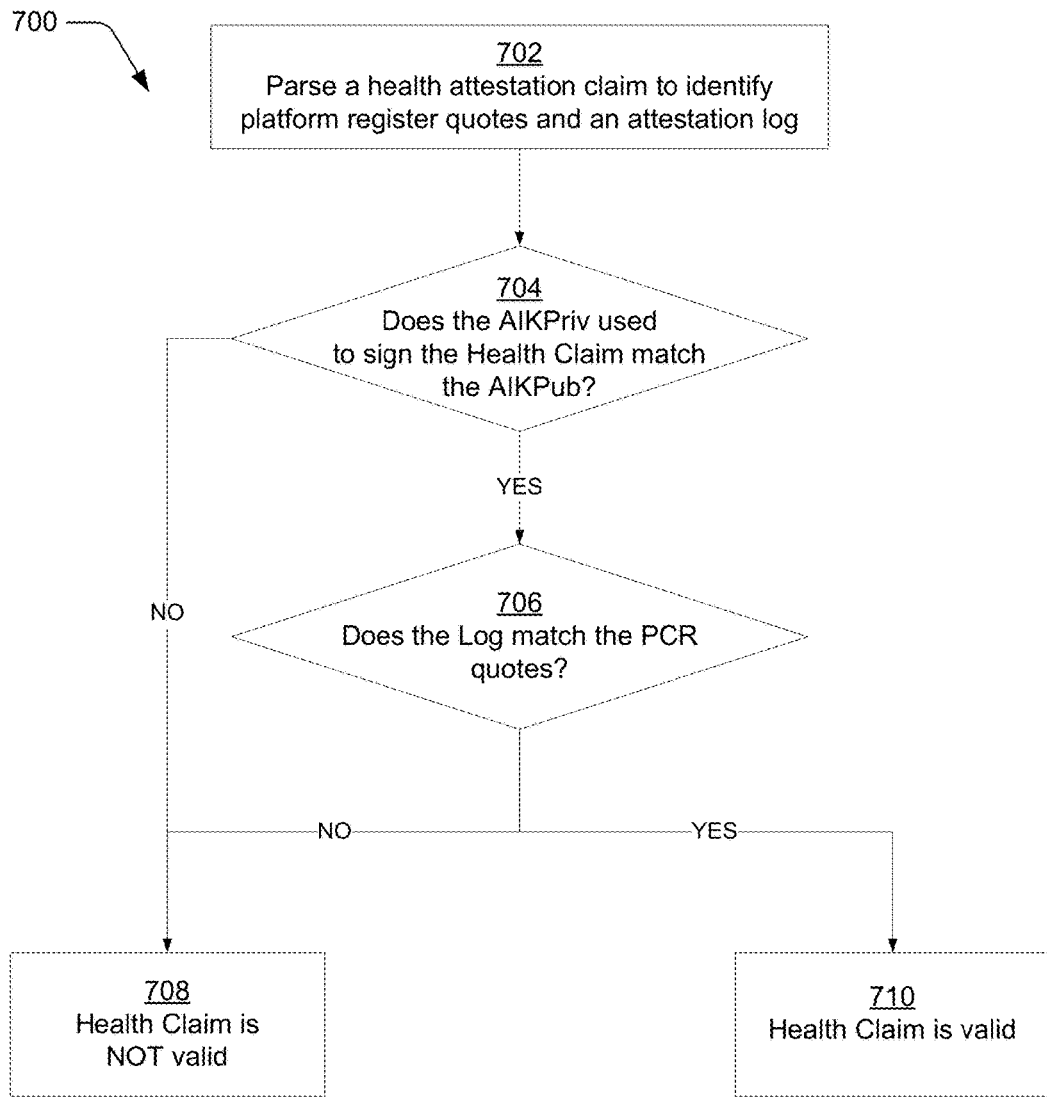
FIG. 7 is a flow diagram that illustrates steps in a method for verifying a health attestation claim in accordance with one or more embodiments of the present invention.

At step 416, the server 130 verifies the health claim as described in detail with regard to FIG. 7. Generally, the server verifies that the signature on the PCR quotes is correct and consistent with the TCG log value by using the AIKPub from the key claim. The AIKPub is not trusted at this point (because the server has not received an AIK Certificate), but the server will check whether the AIKPub exists on the same TPM as the specified EKPub, which is known to be valid based on the EK certificate reviewed in step 411. Also at step 416, the server 130 checks the PCRs in the health claim against the log to make sure that they match. If the verification process 416 determines that the health claim is valid, the health server 130 generates a health certificate at step 420.

If one or more of the EK certificate, the key attestation claim, or the health attestation claim is not verified or determined to be valid at steps 411, 412, or 416, the server 130 denies the request for the health certificate and thus does not generate a health certificate for the client device 102. In at least some implementations, the health service 130 returns a notification to the client device 102 indicating that the request is denied. The notification may also include other information, such as which of the key attestation claim and/or the health attestation claim was determined to be invalid, and why the particular claim(s) was determined to be invalid.

Assuming verification checks 411, 412 and 416 pass, at step 422, the server 130 creates a health blob by encrypting the health certificate with the AES Key and packaging it with the EK Challenge, which includes the AIK 120.

Figure 10:
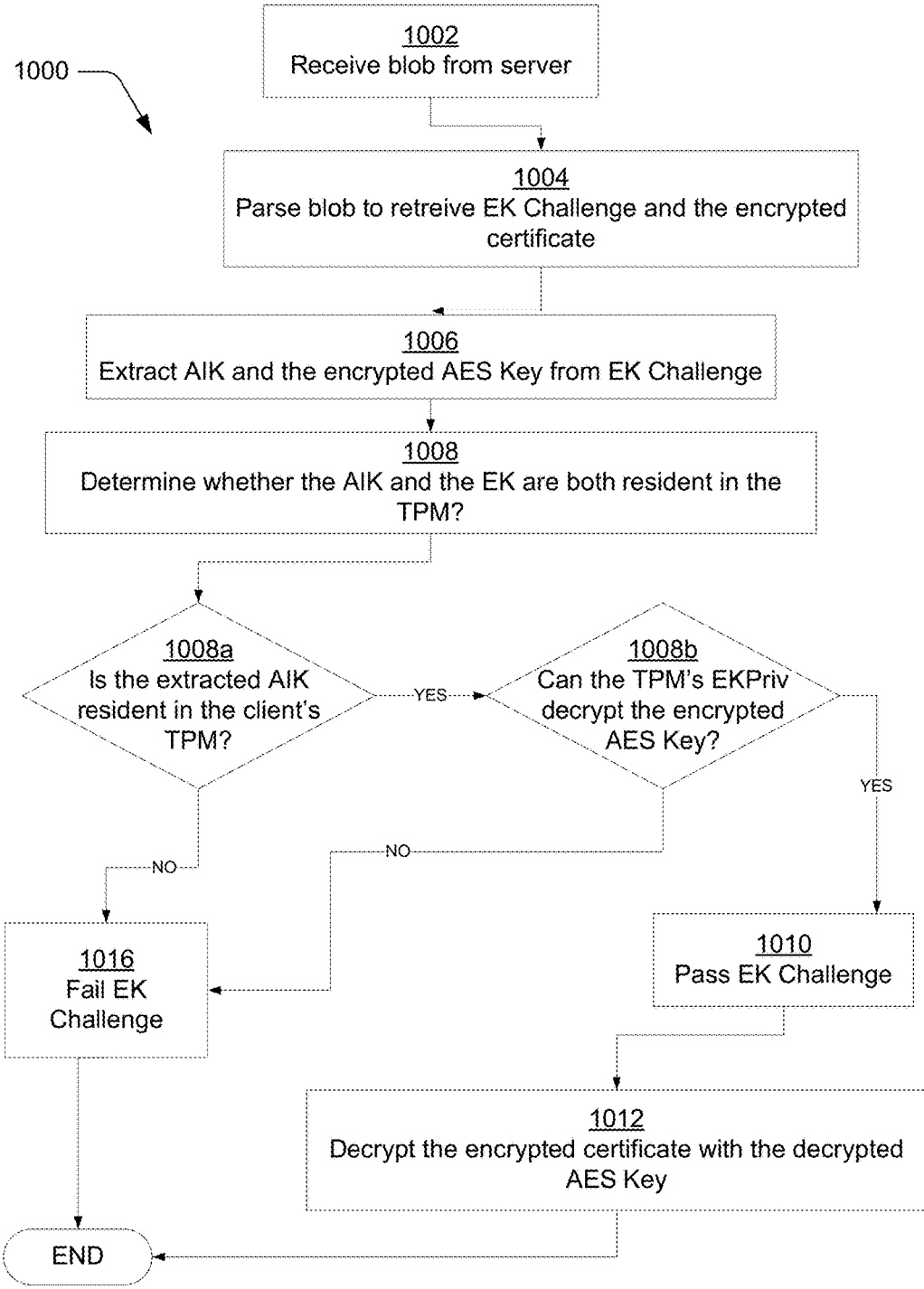
FIG. 10 is a flow diagram that illustrates the steps in a method for a client to evaluate a key challenge (e.g., EK challenge) received from a server in accordance with one or more embodiments of the present invention.

The client's handling of the health blob as shown in steps 424-432 of FIG. 4 is shown in detail in FIG. 10. Continuing to step 424, the health server 130 sends the health blob to the client device 102 at step 424 and the TPM access module 110 parses the health blob to retrieve the encrypted AES Key, the AIK 120, and the encrypted health certificate. In at least some implementations, the health blob represents a single integrated communication from the health service 130 to the client device 102.

At this point the TPM access module 110 cannot decrypt the health certificate because it cannot decrypt the encrypted AES key used to encrypt the health certificate. Accordingly, at step 426 the TPM Access Module 110 sends a decryption request to the TPM 108 that includes the encrypted AES Key (i.e., Encrypted$_{EKPub}$(AES Key)). If the TPM 108 has a private EK (EKPriv) that matches the EKPub used to encrypt the AES Key, it will be able to perform a decryption process 428 to generate the decrypted AES Key. If the TPM is able to decrypt the AES key, it will send the AES Key back to the Access Module 110 at step 430. In an embodiment, the decryption request 426 may also include the AIK 120 (from the EK challenge). As part of decryption process 428, the TPM may also check to make sure that the AIK from the challenge is co-resident in the TPM with the EK used to encrypt (e.g. EKPub) and/or decrypt (e.g., EKPriv) the AES Key. If the TPM is not able to decrypt the AES Key, this means that it failed the EK challenge either because the TPM doesn't have the EK that it told the server it had in connection with the request for a health certificate or the AIK is not in the same TPM as the EK.

When the TPM access module 110 receives the AES Key, it uses it to decrypt 432 the encrypted health certificate. The client device 102 stores the health certificate 220 locally for use in attesting to the health of the current state of the client device 102.

In at least some implementations, the health certificate 220 is boot state sensitive. For instance, if the client device 102 reboots after receiving the health certificate 220, the health certificate 220 may expire. In such a case, the scenario 400 can be reinitiated to obtain a new health certificate based on a current boot state of the client device 102.

Figure 5:
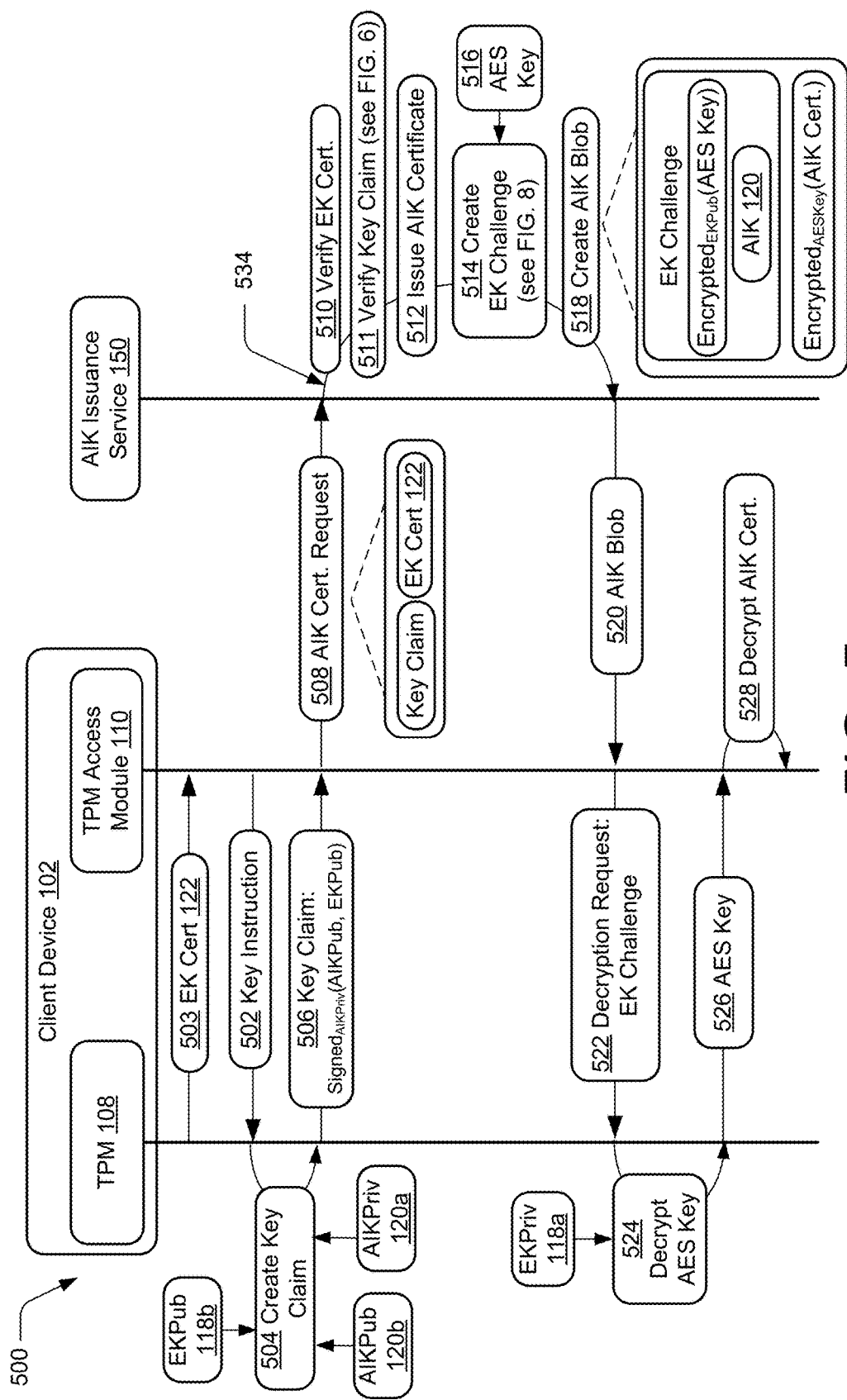
FIG. 5 depicts an example implementation of key attestation in accordance with one or more embodiments of the present invention.

FIG. 5 shows a key attestation process 500 in accordance an embodiment of the present invention. Key attestation process 500 has advantages over the conventional process shown in FIG. 2 because it requires only one hop to a server as shown by arrow 534. Although FIG. 5 shows a request for an AIK certificate (see step 508) made to an AIK Issuance Server 150 and issuance of an AIK certificate, method 500 is not limited to AIK certificates or even certificates in general. It may be used to request any kind of token where there is a need for assurance that token may be accessed/used by the client only if the key attestation is successful (e.g., the client can prove its possession of the EK and the AIK keys in its TPM), thus ensuring no other system can get to the token by hijacking the request and/or the response. Examples of tokens that may be securely passed to clients using method 500 include without limitation decryption keys, signing keys, authentication tokens to login to other systems or web sites, and licenses to enable a certain features on a specific client machine.

At step 502, the TPM access module 110 communicates a key attestation instruction (key instruction) to the TPM 108. Generally, the key instruction instructs the TPM 108 to create a key attestation claim (key claim). In response to receiving the key instruction, the TPM 108 generates the key claim. The key claim includes the public AIK (AIKPub) 120b and the public EK (EKPub) 118b and is signed using the private AIK (AIKPriv) 120a. For instance, the key claim is generated as Signed$_{AIKPriv}$(AIKPub, EKPub). After generating the key claim at step 504, the TPM 108 communicates the key claim to the TPM access module 110 at step 506. The TPM 108 sends the EK certificate 122 to the TPM Access Module 110, either in response to the key instruction or at some earlier point in time. Step 503 and 506 can occur in any order and can be sent together or separately.

At step 508, the TPM 110 sends an AIK certificate request to a server with an AIK Certificate Authority for verification, such as AIK Issuance Service 150. The request includes the key claim and the EK certificate.

At step 510, the server extracts the EK certificate from the AIK certificate request and verifies that the EK cert is issued by a known and trusted CA, that the certificate is valid, and is not revoked. It then extracts the EKPub from the EK certificate.

At step 511, the server 130 verifies the key claim as described in detail with regard to FIG. 6. If the verification step 511 passes, the process 500 proceeds to step 512 where it issues an AIK Certificate.

At step 514, the server creates an EK Challenge, which is described in detail with respect to FIG. 8. Generally, this process includes generating an AES key 516, encrypting this key using the EKPub 118a that was extracted from the EK certificate in step 510, and then packaging this together with the AIK received in the key claim.

At step 514, the server 150 creates an AIK blob that includes the AIK Certificate that is encrypted using the AES Key and which is wrapped in the EK Challenge. The server sends the AIK blob to the TPM Access Module at step 520.

The client's handling of the health blob as shown in steps 520-528 of FIG. 5 is shown in detail in FIG. 10. Generally, the TPM Access Module 110 parses the AIK blob to extract the EK Challenge and sends a decryption request (with the encrypted AES Key and AIK) to the TPM 108 at step 522.

At step 524, the TPM 108 verifies that the AIK is co-resident in the TPM with the EKPub used to sign the EK Challenge. The TPM 108 also tries to decrypt the AES Key using the EKPriv 118a that is resident on the TPM. If the AIK is co-resident with the EK and the TPM 108 is able to decrypt the AES Key using the EKPriv, the client 102 will send the AES Key back to the TPM Access Module 110 at step 526. The TPM Access Module 110 will then be able to decrypt the AIK certificate with the AES Key at step 528. In this way, the client has obtained an AIK Certificate through a process that includes a single round trip (see arrow 534) to the AIK server 150.

FIG. 6 is a flow diagram that describes steps of a method in accordance with one or more embodiments of the present invention. The method 600, for instance, describes an example procedure for verifying a validity of a key attestation claim. In at least some implementations, FIG. 6 illustrates a way for performing aspects of step 412 of FIG. 4 and step 512 of FIG. 5. In embodiments, process 600 is performed by a server, such as server 150 with an AIK Issuance Service or server 130 with a Health Certificate Service.

Process 600 begins at step 602, which verifies a signature of a key attestation claim. The health service 130, for instance, verifies that the signature of key attestation claim Signed$_{AIKPriv}$(AIKPub, EKPub) is valid. It does this by checking to make sure that AIKPub matches the AIKPriv used to sign the key claim. In one embodiment, the AIKPub is extracted from a key claim received by the server. In other embodiments, the AIKPub may have been obtained from another source. If the AIKPub and AIKPriv match ("Yes"), the method 600 proceeds to step 612 where it determines that the key claim is valid. If they do not match, method 600 cannot verify the key claim and proceeds to step 610.

Returning to step 604, the server checks to confirm that the EK certificate it received is from a known and trusted certificate authority, that it is valid, and it is not revoked. If all of these are true ("Yes"), the method 600 proceeds to step 612 where it determines that the key claim is valid. If any one of these are not true ("No"), method 600 cannot verify the key claim and proceeds to step 610.

Although steps 602 and 604 are shown in a particular order, they may be performed in any order for purposes of the present invention.

FIG. 7 is a flow diagram that describes steps in a method 700 in accordance with one or more embodiments of the present invention. The method, for instance, describes an example procedure for verifying the validity of a health attestation claim (e.g., health claim). In at least some implementations, the procedure describes an example way for performing aspects of step 416 of the procedure described above with reference to FIG. 4.

Step 702 parses a health attestation claim to identify platform register (PCR) quotes and an attestation log. As discussed above, the platform register quotes include measurements from known safe portions of code from the client device 102, such as from code modules, binaries, executables, and so forth. The platform register quotes, for instance, represent measurements retrieved from a platform configuration register of the TPM 108. The attestation log represents measurements of code that is loaded and/or running on the client device 102. For instance, when a request for health certificate for the client device 102 is initiated, measurements of code that is loaded and/or running on the client device 102 are captured and stored as part of the attestation log.

Step 704 verifies a signature of the health claim, which is signed using the private AIK 120a, i.e., AIKPriv. Thus, the health service 130 verifies that the platform register quotes are signed with a valid AIKPriv. It does this by checking to make sure that the AIKPub matches the AIKPriv used to sign the key claim. If they match ("Yes"), method 700 proceeds to step 706. If they do not match, method 600 cannot verify the health claim and proceeds to step 708.

Step 706 ascertains whether the attestation log matches the platform register quotes. For instance, the health service 130 compares measurements of code modules included in the attestation log to measurements of corresponding code in the platform register quotes. The health service 130, for example, determines whether a particular measurement from the attestation log for a particular portion of code match a particular measurement for the particular portion of code from the platform registers 126. In at least some implementations, a mismatch between the attestation log and the platform registers 126 can indicate that a portion of code has been tampered with, such as by a hacker, by malware, and so forth. This may indicate that the client device 102 is in an unsafe state, which would cause the attestation claim to fail such that a valid health certificate for the client device 102 is not issued. If the attestation log does not match the platform register quotes ("No"), the method 700 proceeds to step 708 and ascertains that the health attestation claim is not valid.

If the attestation log matches the platform register quotes ("Yes"), the method 700 ascertains that the health attestation claim is valid at 710 and that a process for issuing a health certificate for the client device 102 can proceed.

Although steps 704 and 706 are shown in a particular order, they may be performed in any order for purposes of the present invention.

FIG. 8 is a flow diagram that describes steps in a method 800 in accordance with one or more embodiments of the present invention. More specifically, FIG. 8 illustrates an example method for generating an EK challenge as shown in step 414 in FIG. 4 and step 514 in FIG. 5. In embodiments, process 800 is performed by a server, such as server 150 with an AIK Issuance Service or server 130 with a Health Certificate Service.

Method 800 begins by generating a secret at step 802. In at least some implementations, the secret represents a symmetric cryptographic key (e.g. an AES Key) that can be used for both encryption and decryption of data.

At step 804, the public endorsement key (EKPub) is extracted from the endorsement key certificate. For instance, in one embodiment the health service 130 extracts the EKPub 120b from the EK certificate 122 received from the client device 102 at step 410 of FIG. 4. In another embodiment, the AIK service 150 extracts the EKPub from the EK certificate it received from the client device at step 508 of FIG. 5. In an alternative embodiment, the EKPub may come from another source, such as a key claim.

At step 806, the server encrypts the AES Key using the public EK to form Encrypted$_{EKPub}$(AES Key).

At step 808, the server packages the encrypted AES Key with the AIK (such as the AIKPub and/or AIKPriv) from a key claim or other source to form the EK Challenge.

FIG. 10 is a flow diagram that describes steps of a method in accordance with one or more embodiments of the present invention. The method 1000, for instance, describes an example procedure for receiving and responding to a key challenge, such as the EK challenge described with reference to FIGS. 4 and 5. In at least some implementations, FIG. 10 illustrates a way for performing aspects of steps 424-432 of FIG. 4 and steps 520-528 of FIG. 5. In embodiments, process 1000 is performed by a client, such as client 102.

Method 1000 begins at step 1002, where the client 102 receives a blob, such as a health blob or an AIK blob. At step 1004, the client parses the blob to retrieve the EK challenge and the encrypted certificate. At step 1006, the client extracts the encrypted AES Key (or other server secret) and the encrypted certificate. At this point, the client is not able to decrypt the encrypted certificate because the key it needs is encrypted within the EK Challenge. The client must pass the EK challenge to be able to decrypt the encrypted certificate. To pass the EK Challenge, the client must prove that the AIK extracted from the challenge is co-resident in the same TPM as the EK used to encrypt the server's secret (e.g., the AES Key) (see step 1008).

Determining whether the client will be able to pass the EK challenge occurs in two steps (1008a and 1008b), which may occur in any order. At step 1008a, the client determines whether the extracted AIK from the EK Challenge is resident is the client's TPM by comparing it to the AIK that is resident in the TPM. If they match ("Yes"), the method moves to step 1008b. If they do not match ("No"), the client has failed the EK challenge (step 1016).

Returning to step 1008b, the client attempts to decrypt the server's secret using the EKPriv from the TPM 108. If decryption is successful ("Yes"), the method has passed the EK challenge at step 1010 and proceeds to use the decrypted server secret to decrypt the encrypted certificate at step 1012. If, on the other hand, decryption is not successful ("No" at step 1008b), the method has failed the EK challenge at step 1016.

Figure 9:
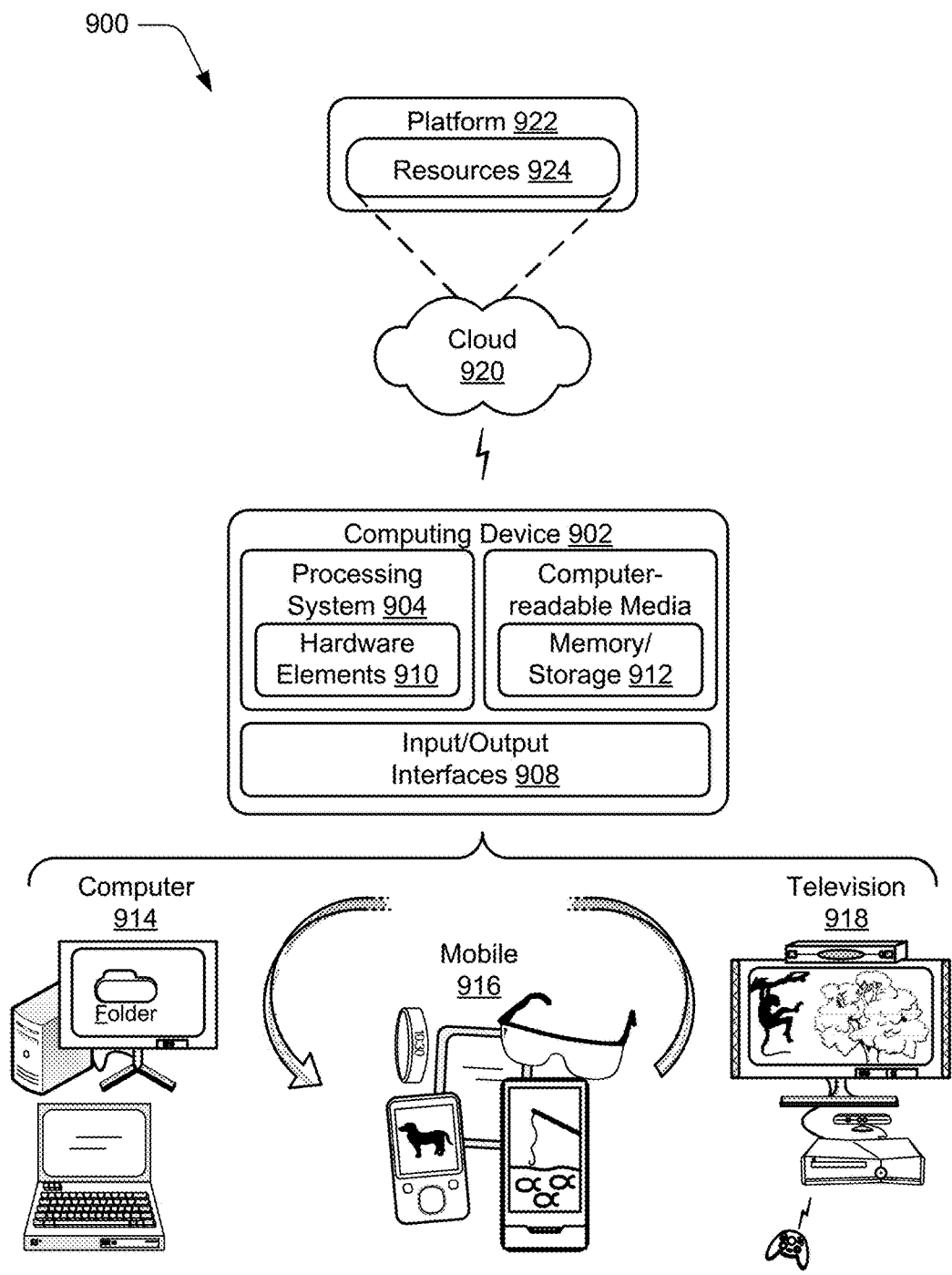
FIG. 9 depicts an example implementation of health certificate based on key attestation and health attestation in accordance with one or embodiments of the present invention.

FIG. 9 illustrates an example system generally at 900 that includes an example computing device 902 that is representative of one or more computing systems and/or devices that may implement various techniques described herein. For example, the client device I 02 and/or the health service 130 discussed above with reference to FIG. 1 can be embodied as the computing device 902. The computing device 902 may be, for example, a server of a service provider, a device associated with the client (e.g., a client device), an on-chip system, and/or any other suitable computing device or computing system.

The example computing device 902 as illustrated includes a processing system 904, one or more computer-readable media 906, and one or more Input/Output (I/O) Interfaces 908 that are communicatively coupled, one to another. Although not shown, the computing device 902 may further include a system bus or other data and command transfer system that couples the various components, one to another. A system bus can include any one or combination of different bus structures, such as a memory bus or memory controller, a peripheral bus, a universal serial bus, and/or a processor or local bus that utilizes any of a variety of bus architectures. A variety of other examples are also contemplated, such as control and data lines.

The processing system 904 is representative of functionality to perform one or more operations using hardware. Accordingly, the processing system 904 is illustrated as including hardware element 910 that may be configured as processors, functional blocks, and so forth. This may include implementation in hardware as an application specific integrated circuit or other logic device formed using one or more semiconductors. The hardware elements 910 are not limited by the materials from which they are formed or the processing mechanisms employed therein. For example, processors may be comprised of semiconductor(s) and/or transistors (e.g., electronic integrated circuits (ICs)). In such a context, processor-executable instructions may be electronically executable instructions.

The computer-readable media 906 is illustrated as including memory/storage 912. The memory/storage 912 represents memory/storage capacity associated with one or more computer-readable media. The memory/storage 912 may include volatile media (such as random access memory (RAM)) and/or nonvolatile media (such as read only memory (ROM), Flash memory, optical disks, magnetic disks, and so forth). The memory/storage 912 may include fixed media (e.g., RAM, ROM, a fixed hard drive, and so on) as well as removable media (e.g., Flash memory, a removable hard drive, an optical disc, and so forth). The computer-readable media 906 may be configured in a variety of other ways as further described below.

Input/output interface(s) 908 are representative of functionality to allow a user to enter commands and information to computing device 902, and also allow information to be presented to the user and/or other components or devices using various input/output devices. Examples of input devices include a keyboard, a cursor control device (e.g., a mouse), a microphone (e.g., for voice recognition and/or spoken input), a scanner, touch functionality (e.g., capacitive or other sensors that are configured to detect physical touch), a camera (e.g., which may employ visible or non-visible wavelengths such as infrared frequencies to detect movement that does not involve touch as gestures), and so forth. Examples of output devices include a display device (e.g., a monitor or projector), speakers, a printer, a network card, tactile-response device, and so forth. Thus, the computing device 902 may be configured in a variety of ways as further described below to support user interaction.

Various techniques may be described herein in the general context of software, hardware elements, or program modules. Generally, such modules include routines, programs, objects, elements, components, data structures, and so forth that perform particular tasks or implement particular abstract data types. The terms "module," "functionality," "entity," and "component" as used herein generally represent software, firmware, hardware, or a combination thereof. The features of the techniques described herein are platform-independent, meaning that the techniques may be implemented on a variety of commercial computing platforms having a variety of processors.

An implementation of the described modules and techniques may be stored on or transmitted across some form of computer-readable media. The computer-readable media may include a variety of media that may be accessed by the computing device 902. By way of example, and not limitation, computer-readable media may include "computer-readable storage media" and "computer-readable signal media." "Computer-readable storage media" may refer to media and/or devices that enable persistent storage of information in contrast to mere signal transmission, carrier waves, or signals per se. Computer-readable storage media do not include signals per se. The computer-readable storage media includes hardware such as volatile and non-volatile, removable and non-removable media and/or storage devices implemented in a method or technology suitable for storage of information such as computer readable instructions, data structures, program modules, logic elements/circuits, or other data. Examples of computer-readable storage media may include, but are not limited to, RAM, ROM, EEPROM, flash memory or other memory technology, CD-ROM, digital versatile disks (DVD) or other optical storage, hard disks, magnetic cassettes, magnetic tape, magnetic disk storage or other magnetic storage devices, or other storage device, tangible media, or article of manufacture suitable to store the desired information and which may be accessed by a computer.

"Computer-readable signal media" may refer to a signal-bearing medium that is configured to transmit instructions to the hardware of the computing device 902, such as via a network. Signal media typically may embody computer readable instructions, data structures, program modules, or other data in a modulated data signal, such as carrier waves, data signals, or other transport mechanism. Signal media also include any information delivery media. The term "modulated data signal" means a signal that has one or more of its characteristics set or changed in such a manner as to encode information in the signal. By way of example, and not limitation, communication media include wired media such as a wired network or direct-wired connection, and wireless media such as acoustic, radio frequency (RF), infrared, and other wireless media. As previously described, hardware elements 910 and computer-readable media 906 are representative of instructions, modules, programmable device logic and/or fixed device logic implemented in a hardware form that may be employed in some embodiments to implement at least some aspects of the techniques described herein. Hardware elements may include components of an integrated circuit or on-chip system, an application-specific integrated circuit (ASIC), a field-programmable gate array (FPGA), a complex programmable logic device (CPLD), and other implementations in silicon or other hardware devices. In this context, a hardware element may operate as a processing device that performs program tasks defined by instructions, modules, and/or logic embodied by the hardware element as well as a hardware device utilized to store instructions for execution, e.g., the computer-readable storage media described previously.

Combinations of the foregoing may also be employed to implement various techniques and modules described herein. Accordingly, software, hardware, or program modules and other program modules may be implemented as one or more instructions and/or logic embodied on some form of computer-readable storage media and/or by one or more hardware elements 910. The computing device 902 may be configured to implement particular instructions and/or functions corresponding to the software and/or hardware modules. Accordingly, implementation of modules that are executable by the computing device 902 as software may be achieved at least partially in hardware, e.g., through use of computer-readable storage media and/or hardware elements 910 of the processing system. The instructions and/or functions may be executable/operable by one or more articles of manufacture (for example, one or more computing devices 902 and/or processing systems 904) to implement techniques, modules, and examples described herein.

As further illustrated in FIG. 9, the example system 900 enables ubiquitous environments for a seamless user experience when running applications on a personal computer (PC), a television device, and/or a mobile device. Services and applications run substantially similar in all three environments for a common user experience when transitioning from one device to the next while utilizing an application, playing a video game, watching a video, and so on.

In the example system 900, multiple devices are interconnected through a central computing device. The central computing device may be local to the multiple devices or may be located remotely from the multiple devices. In one embodiment, the central computing device may be a cloud of one or more server computers that are connected to the multiple devices through a network, the Internet, or other data communication link. In one embodiment, this interconnection architecture enables functionality to be delivered across multiple devices to provide a common and seamless experience to a user of the multiple devices. Each of the multiple devices may have different physical requirements and capabilities, and the central computing device uses a platform to enable the delivery of an experience to the device that is both tailored to the device and yet common to all devices. In one embodiment, a class of target devices is created and experiences are tailored to the generic class of devices. A class of devices may be defined by physical features, types of usage, or other common characteristics of the devices. In various implementations, the computing device 902 may assume a variety of different configurations, such as for computer 914, mobile 916, and television 918 uses. Each of these configurations includes devices that may have generally different constructs and capabilities, and thus the computing device 902 may be configured according to one or more of the different device classes. For instance, the computing device 902 may be implemented as the computer 914 class of a device that includes a personal computer, desktop computer, a multi-screen computer, laptop computer, netbook, and so on.

The computing device 902 may also be implemented as the mobile 916 class of device that includes mobile devices, such as a mobile phone, portable music player, portable gaming device, a tablet computer, a wearable device, a multi-screen computer, and so on. The computing device 902 may also be implemented as the television 918 class of device that includes devices having or connected to generally larger screens in casual viewing environments. These devices include televisions, set-top boxes, gaming consoles, and so on. The techniques described herein may be supported by these various configurations of the computing device 902 and are not limited to the specific examples of the techniques described herein.

The cloud 920 includes and/or is representative of a platform 922 for resources 924. The platform 922 abstracts underlying functionality of hardware (e.g., servers) and software resources of the cloud 920. The resources 924 may include applications and/or data that can be utilized while computer processing is executed on servers that are remote from the computing device 902. Resources 924 can also include services provided over the Internet and/or through a subscriber network, such as a cellular or Wi-Fi network. The platform 922 may abstract resources and functions to connect the computing device 902 with other computing devices. The platform 922 may also serve to abstract scaling of resources to provide a corresponding level of scale to encountered demand for the resources 924 that are implemented via the platform 922. Accordingly, in an interconnected device embodiment, implementation of functionality described herein may be distributed throughout the system 900. For example, the functionality may be implemented in part on the computing device 902 as well as via the platform 922 that abstracts the functionality of the cloud 920.

Discussed herein are a number of methods that may be implemented to perform techniques discussed herein. Aspects of the methods may be implemented in hardware, firmware, or software, or a combination thereof. The methods are shown as a set of steps that specify operations performed by one or more devices and are not necessarily limited to the orders shown for performing the operations by the respective blocks. Further, an operation shown with respect to a particular method may be combined and/or interchanged with an operation of a different method in accordance with one or more implementations. Aspects of the methods can be implemented via interaction between various entities discussed above with reference to the environment 100.

While implementations are discussed herein with reference to obtaining a health certificate, it is to be appreciated that aspects of the techniques can be employed for various other purposes, such as key attestation. Having discussed some example scenarios and procedures for health certificate based on key attestation and Health attestation, consider now a discussion of an example system and device in accordance with one or more embodiments.

What is claimed is:

1. A computer-implemented method for providing a token to a client computer based on TPM key attestation, the method comprising:
   (a) receiving a token request from a client computer, wherein the token request includes a key attestation claim and an endorsement key certificate;
   (b) verifying the key attestation claim;
   (c) extracting a TPM public endorsement key from the key attestation claim;
   (d) generating a secret in response to receiving the token request;
   (e) encrypting the token for the client computer with the secret to form an encrypted token;
   (f) encrypting the secret with the TPM public endorsement key from the key attestation claim to form an encrypted secret; and
   (g) sending the encrypted token with the encrypted secret to the client computer.

2. The computer-implemented method of claim 1 wherein the token comprises an attestation identity key certificate.

3. The computer-implemented method of claim 2, wherein step (g) further comprises:
   (g)(1) extracting an attestation identity key from the key attestation claim;
   (g)(2) creating a key challenge, wherein the key challenge includes the encrypted secret and the attestation identity key; and
   (g)(3) sending the key challenge to the client computer with the encrypted token.

4. The computer-implemented method of claim 3, wherein step (g)(3) further comprises:
   (g)(3)(i) creating an AIK blob that includes the key challenge and the encrypted token; and
   (g)(3)(ii) sending the AIK blob to the client computer.

5. The computer-implemented method of claim 1 wherein step (b) further comprises:
   (b)(1) extracting an attestation identity key from the key attestation claim; and
   (b)(2) determining whether the attestation identity key is associated with a TPM that has the public endorsement key that was extracted from the key attestation claim.

6. The computer-implemented method of claim 1 wherein step (d) is performed before step (c).

7. The computer-implemented method of claim 1 wherein the token comprises a health certificate for the client computer.

8. The computer-implemented method of claim 7 wherein the token request further comprises a health attestation claim.

9. The computer-implemented method of claim 1 wherein step (g) further comprises sending the encrypted token with the encrypted secret to the client computer only when the key claim is verified as valid in step (b).

10. The computer-implemented method of claim 1 wherein the secret is an asymmetrical key.

11. The computer-implemented method of claim 1 wherein the token comprises a secret key.

12. A health service system comprising a health server computer, wherein the health server computer includes a processor in electronic communication with a memory, the memory storing computer-readable instructions that when executed by the processor cause the health server computer to:
 receive a health certificate request, a key attestation claim, and a health attestation claim from a client computer;
 verify the key attestation claim;
 verify the health attestation claim;
 create a health certificate for the client computer;
 generate a server key in response to receiving the health certificate request;
 encrypt the health certificate for the client computer with the server key to form an encrypted health certificate;
 encrypt the server key with a TPM public endorsement key associated with the client computer to form an encrypted server key; and
 send the encrypted health certificate with encrypted server key to the client computer.

13. The health service system of claim 12, further comprising computer-readable instructions stored in the memory that when executed by the processor cause the health server computer to:
 extract an attestation identity key from the key attestation claim;
 create a key challenge, wherein the key challenge includes the encrypted server key and the attestation identity key; and
 send the key challenge to the client computer with the encrypted certificate.

14. The health service system of claim 13, further comprising computer-readable instructions stored in the memory that when executed by the processor cause the health server computer to:
 create a health blob that includes the key challenge and the encrypted health certificate; and
 send the health blob to the client computer.

15. The health service system of claim 14, wherein the client computer is communicatively accessible to the health server computer over a local area network, and wherein the client computer includes a TPM with a private endorsement key and a processor in electronic communication with a memory, the memory storing computer-readable instructions that when executed by the processor cause the client computer to:
 send the health certificate request, the key attestation claim, and the health attestation claim to the health server computer;
 receive the health blob from the server computer;
 decrypt the encrypted server key using the private endorsement key; and
 decrypt the health certificate using a decrypted server key.

16. The health service system of claim 12, wherein the health certificate request, the key attestation claim, and the health attestation claim are received in a single message from the client computer.

17. The health service system of claim 12, wherein the server key is an asymmetrical key.

18. The health service system of claim 12, further comprising computer-readable instructions stored in the memory that when executed by the processor cause the health server computer to:
 receive an endorsement key certificate for the client computer with the health certificate request;
 verify that the endorsement key certificate is valid;
 extract a public endorsement key from the endorsement key certificate; and
 use the extracted endorsement key to encrypt the server key.

19. A computer-implemented method for obtaining a certificate based on TPM key attestation for a client device, wherein the client device includes a TPM with a public endorsement key, a private endorsement key, an endorsement key certificate, and a public attestation identity key, and a private attestation identity key, the method comprising:
 creating a key claim comprising the public attestation identity key and the public endorsement key from the TPM;
 signing the key claim with the private attestation identity key from the TPM; sending a request for a certificate to a certificate issuing service with the key claim and the endorsement key certificate from the TPM;
 receiving a blob from the certificate issuing service, wherein the blob comprises an encrypted server key and an encrypted certificate;
 parsing the blob to retrieve the encrypted server key and the encrypted certificate;
 using the private endorsement key from the TPM to decrypt the encrypted server key; and
 using the decrypted server key to decrypt the certificate.

20. The computer-implemented method of claim 17 wherein the request for a certificate comprises a request for a health certificate and encrypted certificate comprises health certificate.

* * * * *